United States Patent [19]

Egyud

[11] Patent Number: 5,147,652

[45] Date of Patent: Sep. 15, 1992

[54] AUTOBIOTICS AND THEIR USE IN ELIMINATING NONSELF CELLS IN VIVO

[75] Inventor: Laszlo G. Egyud, Woods Hole, Mass.

[73] Assignee: Cell Research Corporation, Newton, Mass.

[21] Appl. No.: 547,983

[22] Filed: Jul. 3, 1990

[51] Int. Cl.⁵ ............................................ A61K 37/22
[52] U.S. Cl. .................................. 424/450; 436/829; 514/675; 514/693
[58] Field of Search ...................... 424/450, 489, 451; 514/693, 675; 568/420; 436/829

[56] References Cited

U.S. PATENT DOCUMENTS

| 4,066,650 | 1/1978 | Egyud | 260/281 G |
| 4,241,046 | 12/1980 | Papahadjopoulos | 424/19 |
| 4,440,740 | 4/1984 | Fix et al. | 424/1.1 |
| 4,529,561 | 7/1985 | Hunt | 264/4.3 |
| 4,844,904 | 7/1989 | Hamaguchi | 424/450 |
| 4,861,588 | 8/1989 | Neurath | 424/89 |
| 4,906,477 | 3/1990 | Kuyono et al. | 424/450 |

FOREIGN PATENT DOCUMENTS

86/01102 2/1986 PCT Int'l Appl. .

OTHER PUBLICATIONS

Nozawa et al. J. Pharma. Sciences 70, p. 385 (1981).
Underwood Proc. Soc. Exp. Biol Med 100, 312 (1959).
Apple Cancer Chemotherapy Reports 52, 687 (1968).
Schenk Pharmazie 45, 747-9 (1990) *Abstract.*
Arndt. Oncology 44, 257 1987 *Abstract.*
Apple & Greenberg, *Cancer Chemotherapy Reports*, 52: 687-696 (1968).
Egyud & Szent-Gyorgi, *Science*, 160: 1140 (1968).
Underwood & Weed, *Proc. Soc. Exp. Biol. Med*, 83: 421-424 (1956).
Tiffany et al., *J. Am. Chem. Soc.*, 79: 1682 (1957).
Nozawa and Fox, *J. of Phar. Sciences*, 70: 385 (1981).
Thornalley, *Biochem., J.*, 269: 1-11 (1990).

Primary Examiner—Thurman K. Page
Assistant Examiner—G. S. Kishore
Attorney, Agent, or Firm—Hamilton, Brook, Smith & Reynolds

[57] ABSTRACT

Physically and chemically latentiated autobiotics are described. The latentiated autobiotics are useful for the treatment or prevention of any disease or condition, which results from the presence of nonself cells in a vertebrate host. Latentiated autobiotics are furthermore useful in suppressing immune rejection processes, as radiosensitizers and as anticoagulants.

5 Claims, 2 Drawing Sheets

AUTOBIOTICS AND THEIR USE IN ELIMINATING NONSELF CELLS IN VIVO

DESCRIPTION

BACKGROUND OF THE INVENTION

All vertebrates have an immune system. A vertebrate with a severely defective immune system will soon die unless extraordinary measures are taken to isolate it from a variety of infectious agents (e.g., bacteria, viruses, fungi and parasites). A properly functioning immune system is able to distinguish "nonself" cells from "self" cells and, therefore, selectively destroys and eliminates nonself cells such as invading organisms, while leaving self cells intact.

However, some nonself cells evade the host's immune system by camouflaging their outer surface with host protein. These camouflaged nonself cells remain and proliferate in the host undetected. Undetected nonself cells are the cause of many diseases, which plague man and animals. For example, cells infected with viral diseases (e.g., AIDS, influenza, measles, mumps, chicken pox, shingles, hepatitis, diabetes) bacterial diseases (e.g., pneumonia, bronchitis, meningitis. cardititis, periodontitis, bovine mastitis) and fungal diseases (e.g., histoplasmosis, blastomycosis, candidiasis), all result from the infection and proliferation of nonself cells in a host vertebrate.

In addition, cancer results when a vertebrate's own cells become nonself. Healthy individuals at any given moment carry about 50,000–100,000 nonself, potentially malignant cells in their body. These nonself cells are generally recognized and killed by the individual's immune system. However, if any of the nonself cells become camouflaged, they will proliferate as cancer.

Currently, there are not adequate and specific therapies for most diseases that result from the presence of nonself cells in a host. For example, cancer is currently treated either by surgical excision of tumors or by therapies using radiation and highly toxic chemicals. However, surgical excission is not an effective method of treatment where the cancer has metastasized. In addition, radiation and chemotherapy are nonspecific. Therefore, normal cells are often killed in addition to cancerous cells.

Another problem is that the cell-kill caused by chemotherapeutic agents follow first-order kinetics. As a result, a constant percentage, rather than a constant number of cells is killed by a given application of a chemotherapeutic agent. To illustrate, if a drug capable of killing 99.99% of malignant cells is administered to a patient, who harbors $10^{12}$ malignant cells, $10^8$ malignant cells would remain. Although the patient would be diagnosed as having a complete clinical remission, any of the $10^8$ malignant cells remaining could cause a relapse in the disease.

Still another problem with cancer therapies and therapies for other diseases based on the presence of nonself cells in a host is that the nonself cells constantly become resistant to a particular therapeutic agent over time. Attempts to overcome this problem have resulted in protocols whereby several therapeutic agents are used concurrently or in rational sequences. Other protocols are aimed at targeting the drugs more specifically to the nonself cells.

A chemotherapeutic agent that could be used to specifically eliminate nonself cells, but not self cells in vivo would be very useful in treating cancer and a variety of other diseases that result from the presence of nonself cells in a host.

Alpha-ketoaldehydes, a series of chemicals containing the alpha-ketoaldehyde radical, are known as potent inhibitors of the proliferation of nonself cells. The antiviral properties of alpha ketoaldehydes have been intensively and systematically examined and the results published in a series of papers (Underwood, G.E. and S.D. Weed, *Proc. Soc. Exp. Biol. Med.*, 93:421–424 (1956); Tiffany, B.D. et al. *J. Am. Chem. Soc.*, 79:1682 (1957); Underwood. G.E. et al., *Proc. Soc. Exp. Biol. Med.*, 100:312 (1959)). Alpha-ketoaldehydes have also been shown to have a bacteriostatic effect. (Freedberg, W.B. et al. *J. Bacteriol.*, 108:137 (1971); Barrett, P.A. et al. *Nature*, 206:1340 (1965); Egyud, L.G. and A. Szent-Gyorgy, *Proc. Natl. Acad. Sci., USA*, 55:388–393 (1966)). In addition, topical treatment of tumor growth with alpha-ketoaldehydes cures the host (Apple, M.A. and D.M. Greenberg, *Can. Chem. Ther. Rep.*, 51:455–464 (1967); Egyud, L. and A. Szent-Gyorgy, *Science*, 160:1140 (1968); Jerzykowski, T. et al., *Neoplasma*, 17:25–35 (1970)).

However, alpha-ketoaldehydes exhibit a relatively high toxicity in animals. Moreover, they are readily metabolized to the corresponding $\beta$-hydroxy acids by glyoxalase enzymes, which are present in all living cells, especially red blood cells. Therefore, although free alpha-ketoaldehydes inhibit the proliferation of nonself cells, systemic doses of alpha-ketoaldehydes have not been used therapeutically.

SUMMARY OF THE INVENTION

The present invention relates to a class of modified chemicals known as latentiated alpha ketoaldehydes, which can be administered to a vertebrate to specifically eliminate nonself cells in vivo while leaving self cells intact. Alpha-ketoaldehydes can be latentiated by chemical means, physical means or both. Unlike free alpha-ketoaldehydes, latentiated alpha-ketoaldehydes retain biological activity in vivo and can be administered in doses that are nontoxic to the host vertebrate.

In one embodiment, alpha-ketoaldehydes are physically latentiated by entrapment within an encapsulant such as a liposome. An advantage in administering physically latentiated alpha-ketoaldehydes is that there is a high therapeutic index. Also, when administered in vivo, physically latentiated alpha-ketoaldehydes more specifically aggregate at nonself cells. Further, physically latentiated alpha-ketoaldehydes are able to penetrate the blood/brain barrier and, therefore, can be used to treat diseases resulting from the presence of nonself cells in the brain of a host.

Once localized at the nonself cell, there are two modes by which latentiated alpha-ketoaldehydes attack in vivo. In one mode, latentiated alpha ketoaldehydes remove and prevent reformation of the protein coating "camouflaging" the nonself cell. Once the shield is removed, the nonself cell is exposed to foreign cell recognition and destruction by the host's natural killer cells. In another mode, latentiated alpha-ketoaldehydes inhibit protein synthesis and thereby prevent growth and proliferation of the nonself cell.

An important advantage in the use of alpha-ketoaldehydes for controlling cancer or for limiting the proliferation of any nonself cell is that these chemicals do not directly kill the nonself cells, nor do they have a direct effect on the host immune system. As a result, therapy using latentiated alpha-ketoaldehydes is specific (i.e., does not harm host (i.e., self cells)). In addition, this mode of treatment is resistant to mutations. Therefore, potentially all nonself cells can be killed.

Latentiated alpha-ketoaldehydes are furthermore useful as radiosensitizers. In addition, latentiated alpha-ketoaldehydes can be administered to suppress the immune rejection processes of tissue transplantation and as an anticoagulant.

DETAILED DESCRIPTION OF THE INVENTION

Figure 1:
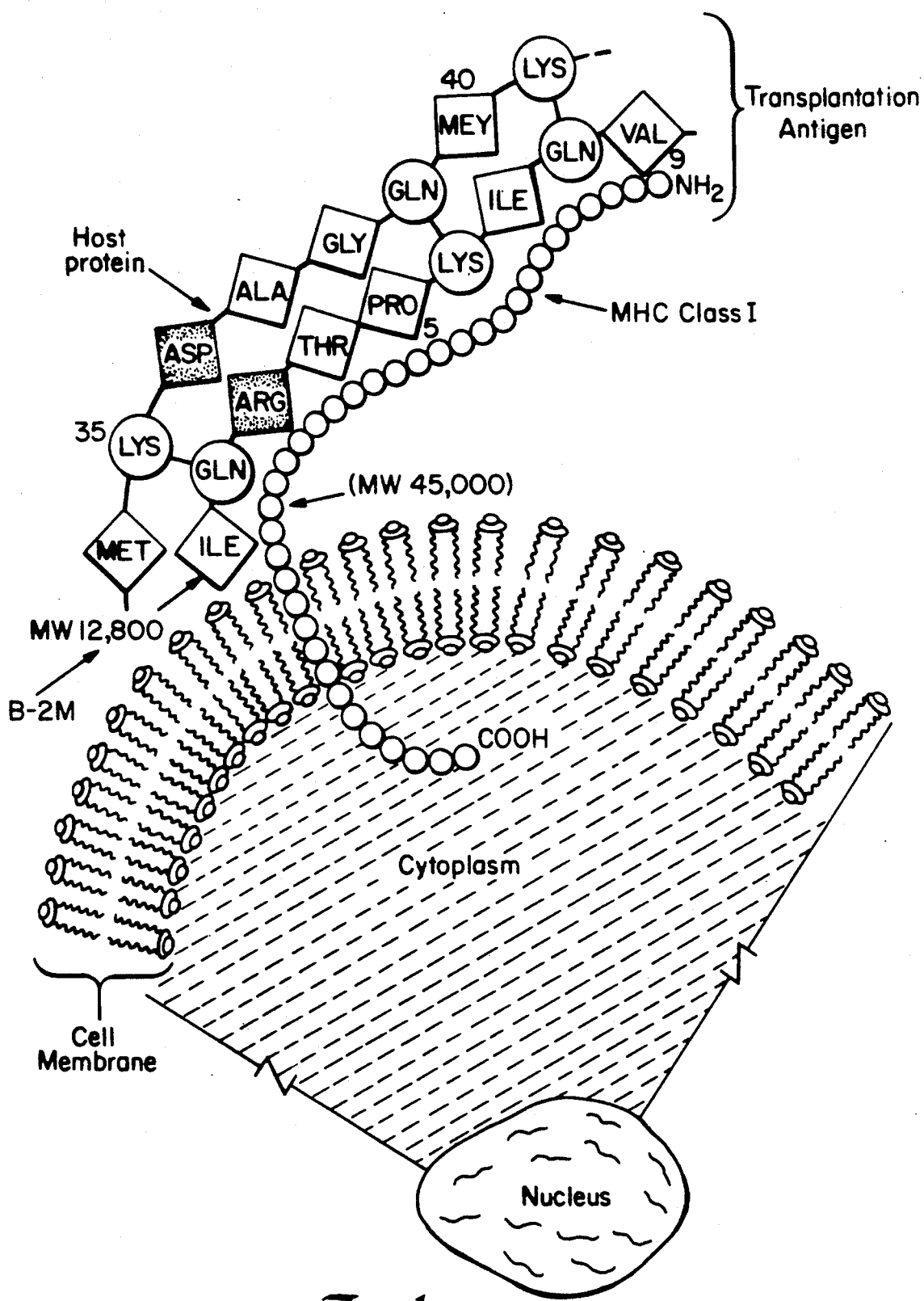
FIG. 1 is a diagram representing the attachment of host protein to the transplantation antigen of a nonself cell.

The present invention is based on the findings that latentiated alpha-ketoaldehydes administered in vivo undergo specific reactions with camouflaged "nonself" cells. For the purpose of the subject application, a nonself cell is defined as a cell present within a vertebrate host, which is different from the host ("self") cell. This difference is expressed on the exterior of the cell via transplantation antigens. Thus, the transplantation antigens of nonself cells differ from the transplantation antigens of host, self cells. Examples of nonself cells include cancer cells, bacteria- or viral-infected cells, fertilized eggs and cells of lower organisms such as fungi, protists, and bacteria.

In one reaction, latentiated alpha-ketoaldehydes remove and prevent the formation of the host protein coating that camouflages nonself cells. Once this coating is removed, the natural killer cells of the host's immune system are able to recognize and kill the nonself cells.

In another reaction, latentiated alpha-ketoaldehydes block protein synthesis, thereby inhibiting cell division. The lower homologues of alpha-ketoaldehyde (i.e.: the aliphatic C-3 and C-4 homologues) may penetrate the cell wall and inhibit protein synthesis from within. The higher homologues (i.e.: above C-5 of the aliphatic series) which do not penetrate the cell surface, together with the lower homologues can block protein synthesis of a dividing cell by reacting with an arginine rich protein. This protein appears on the cell surface at the initiation of cell division and is essential for cell division. (Stein, S.M. and Berestecky J.M. : Cancer Res.:34: 3112 (1974); Stein S.M. and Berestecky J.M.: Cell Physiol:85: 242 (1975)).

As a result of these findings, it is now possible to use latentiated alpha-ketoaldehydes in therapies for treating diseases and conditions resulting from the presence of nonself cells in a vertebrate host. The following is a description of alpha-ketoaldehydes, methods of latentiating alpha ketoaldehydes, and the mechanisms by which alpha-ketoaldehydes act in inhibiting the proliferation of nonself cells in a vertebrate host.

Alpha-ketoaldehydes

Alpha-ketoaldehydes are a series of chemicals derived from glyoxal (CHO-CHO), a dialdehyde with two carbon atoms. The simplest alpha-ketoaldehyde, methylglyoxal (2-oxopropanol), occurs naturally inside normal cells. It is continually formed from several metabolic sources (Ohmori S, et al. "Biosynthesis and Degradation of Methylglyoxal in Animals" in Enzymology and Molecular Biology of Carbonyl Metabolism 2, (Ed: Flynn T.J.) Allan R. Liss Inc. Publisher pages 397–412 1989). Within a cell, alpha-ketoaldehydes function in regulating cell division. Based on this involvement in internal self regulatory process of cell division, alpha-ketoaldehydes have been termed "autobiotics." (Egyud, L.G., *J. Biochem.*, 96:19c (1965); Egyud, L.G., *Proc. Natl. Acad. Sci., USA*, 54:200 (1965)).

Methylglyoxal ($CH_3$-CO-CHO), with three carbon atoms (C-3). is the first member of an aliphatic series where each consecutive member is extended by a —$CH_2$— unit (i.e., C-4, ethylglyoxal $CH_3$—$CH_2$—CO—CHO; C-5, propylglyoxal $CH_3$—$CH_2$—$CH_2$—CO—CHO; etc.). Members of the aliphatic series up to C-5 are soluble in water or lipid solvents. The higher members of the series (C-6 to C-12) are solids and soluble only in organic solvents. The rest of the synthetic compounds are reasonably soluble in water or a mixture of water/organic solvent.

Alpha-ketoaldehydes can be synthesized from the corresponding aldehydes or 2-ketones selenious acid oxidation of N. Rabjohn (*Org. Reactions:*5:332.1949) and H.L. Riley et al. (JCS.: 1932: 1875), by hydrolysis of alpha-oximino ketones (*Cox;JCS.:*1936: 129, Taylor, *JCS.,:*1926: 2822) or by cupric acid oxidation of 2-keto alcohols (Christaensen et al., *Chem. Ind.* 1259, (1958) or U.S. Patents in *Chem.Abst.*51: 2072b 1957, ibid 51: 7446. 1957, Florkin, *Stotz Comphenz. Biochem.* 10: 85 1963). The alpha-ketoaldehydes can then be isolated by fractional distillation. The pure product, in cis- and transform, can be obtained by preparative gas chromatography. A number of alpha-ketoaldehydes (e.g., methylglyoxal, phenylglyoxal and hydroxymethylglyoxal) are also commercially available. Beta-substituted alpha-keto-butyraldehydes are available under the tradenames "Kethoxal" and "Methoxal."

For the purposes of the subject invention, "alpha-ketoaldehyde" refers to a series of chemicals containing the aldehyde radical sequence attached to a greatly variable structure. Over 30 alpha ketoaldehyde containing aliphatic, aromatic, heterocyclic, polycyclic moieties were synthesised and are described in U.S. Pat. No. 4,066,650, entitled "Keto-Aldehyde-Amine Addition Products and Method of Making Same". The teachings of the Egyud patent are incorporated by reference herein. The preferred alpha- ketoaldehydes, however, without limitation include methylglyoxal, phenylglyoxal and chlorinated derivatives, such as, chloromethylglyoxal, dichloromethylglyoxal, chlorophenylglyoxal and dichlorophenylglyoxal.

Latentiation

Alpha-ketoaldehydes present on the exterior of vertebrate cells are relatively toxic. Moreover, they are readily metabolized intracellularly to the corresponding β-hydroxy acids by glyoxalase enzymes in the presence of glutathione, which are present in all living cells (e.g., animal, plant, bacterial cells). Glyoxalase enzymes are especially active in red blood cells. However, alpha-ketoaldehydes can be modified so that they are protected against the action of glyoxalases while at the same time their in vivo toxicity is decreased and their specificity enhanced.

"Latentiation" refers to chemical or physical means of protecting the aldehydic function of alpha-ketoaldehydes against significant modification or destruction by the in vivo environment. Latentiated alpha-ketoaldehydes, therefore, remain in a patient's blood stream longer than free alpha-ketoaldehydes.

Applicant has determined the half life of free and latentiated alpha-ketoaldehydes by injecting methylglyoxal radiolabelled with $C^{14}$ into mice. The in vivo decomposition of both free and latentiated methylglyoxal was followed by the appearance of radiolabelled $C^{14}$, which can be detected in the respiratory air or in urine of the mice. With free alpha-ketoaldehydes, the half-life is about 30 minutes. However, the half life of latentiated alpha-ketoaldehydes is extended to at least 12 hours. Latentiation also protects host cells from the toxic effects of alpha-ketoaldehydes.

Latentiation can be accomplished chemically, physically or both chemically and physically. For example, U.S. Pat. No. 4,066,650, entitled "Keto-Aldehyde-Amine Addition Products and Method of Making Same" by L.G. Egyud, describes chemically latentiated alpha-ketoaldehydes comprising addition products of mono substituted keto-aldehydes with a secondary amine.

Alpha-ketoaldehydes can also be chemically latentiated on reaction with primary amines. In these monosubstituted derivatives, only the aldehydic function is involved in an addition-type reaction. The formed "aldimine" proceeds further in anhydrous conditions to a labile "Schiff's-base" containing an azomethine linkage. The azomethine linkage due to its environmentally weakened amino group disassociates readily to the parent compounds. The aldimine which formed rapidly under acid catalysis in water can liberate the ketoaldehyde in vivo upon the action of nonspecific amidases.

However, the aldimine molecules are subject to uncontrollable polymerization forming a cyclic triazine derivative in water even at neutral pH and low temperature. The cyclic derivative is stable. There is no enzyme known to exist to decompose the cyclic structure. The chemical structure and purity of chemically latentiated alpha-ketoaldehydes can be verified by physical methods such as but not limited to CHNO analysis, melting point, boiling point, visible-spectroscopy, uv-spectroscopy, liquid chromatography. IR-spectroscopy, nuclear magnetic resonance, mass spectroscopy, thin layer chromatography, high pressure liquid chromatography and gas chromatography.

An example of a physically latentiated alpha-ketoaldehyde is an alpha-ketoaldehyde entrapped in an encapsulant. Examples of encapsulants include liposomes, starches and tissue compatible synthetic chemicals (e.g. plastics). Encapsulants provide a controlled release of alpha-ketoaldehyde over an extended period of time. For example, the release of methylglyoxal from a polymethylmethacrylate encapsulant is complete only after about 175 hr. (Nozawa, Y. and S.W. Fox, *J. Pharm. Sci.*, 70:385-386 (1981)). This controlled release to specific sites (i.e., homing) limits the concentration of free alpha-ketoaldehyde in the blood stream at any point in time and therefore prevents toxic side effects and metabolization.

Liposomes are a preferred encapsulant. Liposomes are formed from water insoluble polar lipids (e.g., phospholipids) in the presence of excess water. The highly ordered assemblages are arranged in a system of concentric closed membranes of an unbroken biomolecular sheet of lipid molecules separated from each other by water molecules. Liposomes may be prepared by a variety of techniques (Szoka, F., Jr. et al., *Ann. Rev. Biophys. Bioeng.*, 9:467(1980); Willschut, J. in Liposome Methodology, eds. Laserman, L.E. and J. Barbet, *INSERM, Paris*, p. 11 (1982)). Depending on the procedure used for preparation, liposomes consist of one or more lamellae. All liposomes, whether multilamellar or unilamellar, enclose an aqueous phase in which water-soluble substances can be encapsulated and released at variable rates. Alternatively, lipid soluble substances or water soluble molecules with hydrophobic moieties can be incorporated in the lipid phase of the liposome.

Liposomes may be prepared from a variety of amphiphilic lipids. The most commonly used are the phospholipids, which are major components of biological membranes. The amphiphilic nature of phospholipids, (i.e., the combination of a polar head and a hydrophobic tail within one molecule), is responsible for the bilayer arrangement upon hydration, where the hydrophilic heads are localized in both the outer part of the bilayer and the hydrophobic fatty acid chains are aligned directly opposite to each other in the inner part of the bilayer. Although any amphiphilic lipid alone is sufficient for the formation of liposomes, the properties of the liposome can be improved by incorporating other water insoluble compounds into the structure. Therefore, liposomes may differ in dimensions, composition, charge (e.g., neutral, positive or negative) and structure (e.g., multilamellar, unilamellar).

Examples 1 and 2 of the subject invention describe in detail methods of making liposomal alpha-ketoaldehydes. For the purposes of the subject invention, optimal liposomes should have a selected size between about 0.02-25 microns. However, liposomal alpha-ketoaldehydes can vary in composition and structure.

Liposomes injected into the body normally accumulate in the liver and spleen. Researchers have found that liposomes also congregate at sites of inflammation (Ostro, M.J and P.R. Cullis, *Am. J. Hosp. Pharm.*, 46:1576-1587 (1989). At sites of infection, inflammation and tumors, the body's vasculature is imperfect and broken up. So it is possible that liposome particles leak out of the circulation and become trapped in the surrounding tissue. It is thought that at this location, cells (e.g., macrophages) dispose of the liposome particles (Mertz, E.T., *Biotechnology*, Vol. 5, Page 6 (1987)).

Although sites in the body where nonself cells occur may also be sites of inflammation, when liposomal alpha-ketoaldehydes are injected in vivo, they have been found to specifically accumulate near nonself cells, in a degree greater than the degree to which liposomes not containing alpha-ketoaldehydes accumulate.

One explanation for the enhanced aggregation of liposomal alpha-ketoaldehydes in the vicinity of nonself cells is electronic attraction. Preparation of liposomes in the presence of alpha-ketoaldehydes results in alpha-ketoaldehydes being "encapsulated" in the interior aqueous phase and also "incapsulated" in the lipid phase. Incapsulation produces —CO—CHO groups, projecting out from the lipid surface. The —CO—CHO groups have a net positive charge. Therefore, these groups may act as a "homing" device, directing the alpha-ketoaldehyde laden liposome to the surface of the nonself cell surface attracted by the highly reactive negatively charged —SH groups (Mehrishi J.N. and D.R. Grassetti, *Nature* 224:563-564 (1969); Mehrishi J.N. *Progress in Biophys. and Mol. Biol.*, 25:3 (1972). The attached liposomes can then enter the nonself cell by pinocytosis or fusion, whereupon the alpha-ketoaldehyde is liberated from the lipid membrane.

Enhanced delivery of other bioactive water soluble molecules to nonself cells can be accomplished by incorporating the biomolecules into the aqueous phase of a liposomal alpha-ketoaldehyde.

Mechanism of Action of Latentiated Alpha-ketoaldehydes

The aldehydic function of an alpha-ketoaldehyde can react with thiol or amino groups. The ketonic function of an alpha-ketoaldehyde reacts with these same groups but to a lesser degree. The reaction of alpha-ketoaldehydes with thiols results in hemimercaptals, while reaction with primary amines results in very unstable aldimines or Schiff's bases. In proteins and nucleic acids, alpha-ketoaldehydes react with the guanidine radical of arginine, the 5-amino group of lysine and the sulphydryl group of cysteine (Shauenstein, E. et al., *Aldehydes in Biological Systems,* Pion Ltd., London, p. 115 (1977)). The reactions that occur between alpha-ketoaldehydes and proteins lead to the deactivation of certain enzymes, in particular, sulphydryl enzymes (Shauenstein, E. et al., id; p.5).

Reactions between alpha-ketoaldehydes and cellular proteins result in a variety of important cellular changes. For example, alpha-ketoaldehydes inhibit cell proliferation primarily by reacting with the functional sulphydryl groups involved in protein biosynthesis (Shauenstein, E. et al., *Aldehydes in Biological Systems,* Pion Ltd., London, p. 122 (1977)). Strong inhibition of protein synthesis by alpha-ketoaldehydes occurs in vitro at concentrations which do not influence cell respiration or intermediary metabolism. The length of inhibition is dependent on the ratio of the cell number to the amount of alpha-ketoaldehyde present in the medium (Otsuka, H. and L.G. Egyud, *Can. Res.,* 27:1498 (1967); (Otsuka, H. and L.G. Egyud, *Curr. Mod. Biol.,* 2:106 (1968)). Inhibited cells resume division upon addition of thiol containing compounds (e.g., 1, 2 dithioethane, British antileusite (BAL), cysteine) but not with glutathione, suggesting the involvement of cellular SH radicals in the inhibitory process.

Inhibition of cell division is probably also due to reactions between alpha-ketoaldehydes and arginine-rich proteins that appear on the surface of cells during the S and G-2 phases of mitosis (Stein, (1974); Stein, S.M. and J.M. Berestecky, *J. Cell Physiol.,* 85:243 (1975)). Stein and co-workers found that reacting phenylglyoxal, an alpha-ketoaldehyde that cannot enter cells with the arginine-rich proteins, results in cells that can not divide, and which become leaky and die.

All of the alpha-ketoaldehydes tested thus far have been found to inhibit cell division in varying degrees indicating that the biological activity rests with the —CO—CHO function. The cell surface is the primary site for inhibition of cell division by alpha-ketoaldehydes which cannot penetrate the cell membrane (i.e., homologues above C-5 of the aliphatic series). Their inhibitory effect on cell division is entirely dependent on reactions with cysteine, arginine, lysine and histidine residues on the cell surface. The lower homologues of the aliphatic series (e.g., C-3 and C-4) penetrate the cell wall. Their inhibitory effect may depend both on the exterior and the interior receptors of the cell. Inhibition of cell proliferation by alpha-ketoaldehydes has been shown for a number of bacteriums, molds, yeast, plants and animal cells in tissue culture.

Cancer cells have been found to be 10–12 times more sensitive to inhibition by alpha-ketoaldehydes than normal cells (Shapiro, R., *Ann. NY Acad. Sci.,* art. 2, p. 624 (1969)). This may be due to the fact that cancer cells have excess amino and thiol groups on their surface (i.e., more than dividing normal cells).

For cell division, the physical status of the cell changes involve both the interior and the membrane of the cell. Because of decreased cohesion, due to liberation of —SH radicals from —S—S— linkages, the interior of a cell becomes semi-liquid so that the inner components can move and rearrange themselves. At the same time, the cell membrane also changes. The cell surface becomes repulsive in order to be able to move independently of the surrounding cells. The dividing cell surface changes so as to break the intercellular disulfide bonds to —SH which detach the dividing cell from the adjoining cells. For normal cells, after cell division is completed, the interior and cell surface revert to the activity level and structure that existed before cell division. As a result, cells formed from the division reattach with the adjacent cells and the surface bonds return to the normal values.

However, if a cell becomes malignant for any reason, the cell does not revert to the normal state after division. This means that the surface of cancer cells do not have the normal attachment properties. As a result, the cancer cell is free to metastasize and move around to other locations or organs in the body. In addition, because nonself cells are unattached, they also have more free —SH groups on their surface (Mehrishi, J.N. and D.R. Grassetti, *Nature,* 224:563-564 (1969); Mehrishi, J.N., *Progress in Biophys. and Mol. biol.,* 25:3 (1972)).

The presence of viruses or bacteria in cells is similarly correlated with an increased number of —SH groups on the surface of an infected cell. In fact, all nonself cells have excess amino and thiol groups on their cell surface. Therefore, nonself cells are much more sensitive to inhibition by alpha-ketoaldehydes than self cells. This fact probably contributes to the high therapeutic index of latentiated alpha-ketoaldehydes.

Cells which are either invaded by microorganisms (i.e., bacteriums, viruses, etc.) or cells which for various reasons have altered cell surfaces (e.g., cancer cells, fertilized eggs) are "foreign" or "nonself" to the host. Altered or nonself cells are routinely recognized as foreign in vivo, and are normally marked, destroyed and eliminated by cells of the Immune Surveillance System (ISS). However, some nonself cells resist the immune system of a host by attaching host protein to their "foreign", transplantation antigenic site.

FIG. 1 is a diagram representing the attachment of host protein to a nonself cell's transplantation antigen. Although the figure only depicts one transplantation antigen, a cell usually contains many such sites. The transplantation antigen is made up of two proteins: Beta-2-microglobulin (B-2-M); and the major histocompatibility complex I (MHC-Class I). The B-2-M is electronically (i.e., via Van der Waal's forces) associated with the MHC-Class-I of the host cell. The host protein is attached to the B-2-M by covalent isopeptide linkages between the gamma carboxylic group of glutamic acid and the epsylon amino group of lysine. The isopeptide linkages between the adjacent protein chains are formed by the action of tissue transglutaminase present in the cell membrane. The attachment of host protein to the transplantation antigen "camouflages" the nonself cell so that it is not recognized by the natural killer cells (NK) of the host's immune system.

Figure 2:
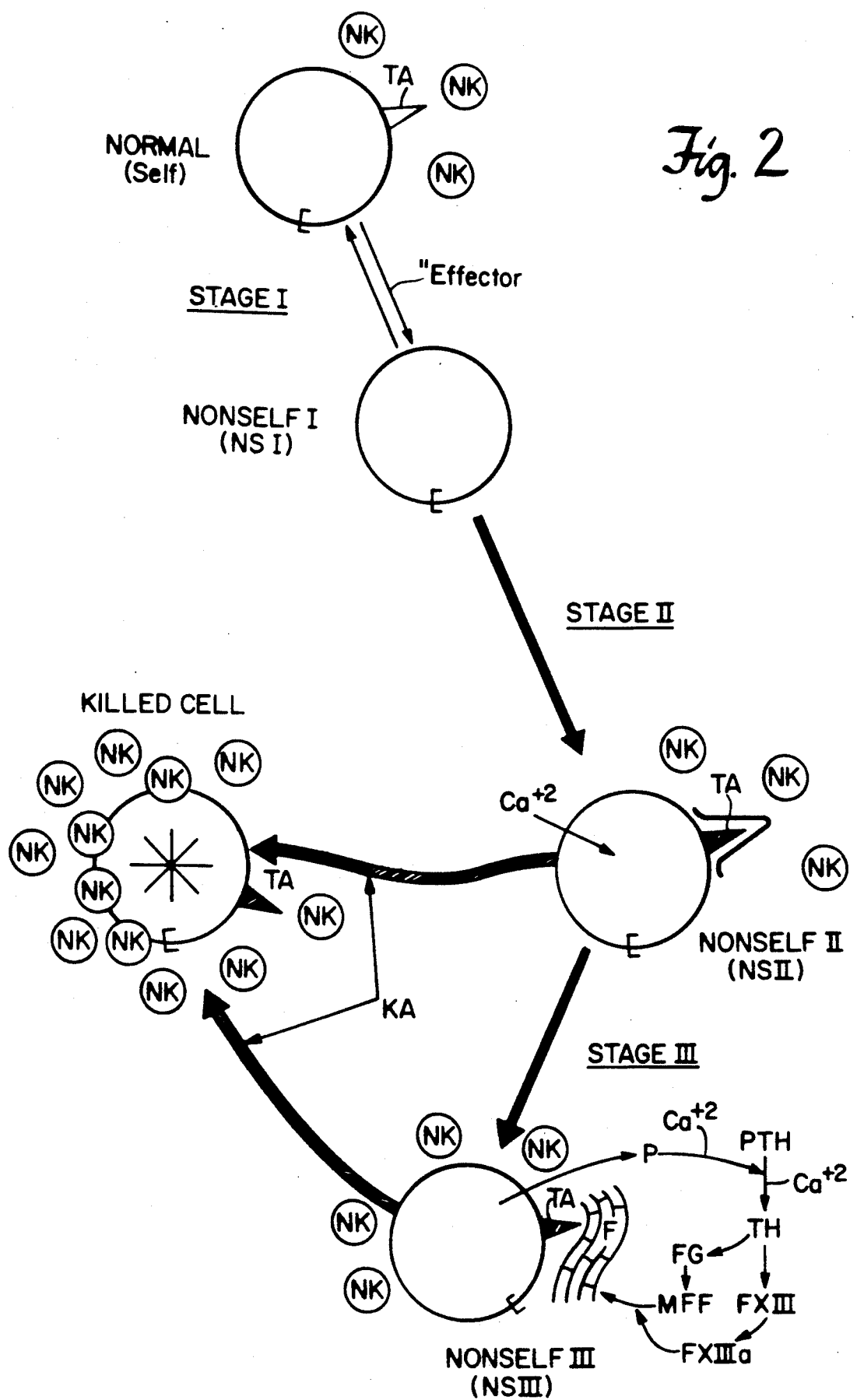
FIG. 2 is a diagram representing the camouflaging of a nonself cell with host protein and the removal of the camouflage upon reaction with an alpha-ketoaldehyde.

FIG. 2 is a diagram representing the camouflaging of a nonself cell and the removal of the camouflage upon reaction with an alpha-ketoaldehyde. Stage 1 of FIG. 2 shows a self cell that is made Nonself I (NS I) by interaction with an "effector." An effector can be a viral, bacterial or fungal pathogen, a cancer causing agent or sperm where the nonself cell is a fertilized egg.

The difference between a nonself cell and a self cell is expressed in the transplantation antigens (TA). Host natural killer cells (NK) generally recognize the different transplantation antigens of nonself cells. Thus, the natural killer cells specifically kill nonself cells.

However, the Nonself I (NS-I) cell may escape recognition by being short lived (i.e., normal cell during cell division (45 min)) or by becoming camouflaged. The cell camouflage is accomplished in two distinct steps. In the first irreversible step (stage 2 of FIG. 2), tissue transglutaminase (E), an enzyme present in the cell membrane activated by calcium ion influx, attaches any available host protein to the B-2-M (depicted in FIG. 1), transforming the cell to Nonself II (NS-II). The attached host protein hides the recognition sites from the natural killer cells, so the cell is not recognized as "foreign".

However, a single protein coat, as occurs in NS-II cells, may not protect cells well enough against highly active killer cells. Therefore, a fortified cell coat is made of multilayered protein. In the second step, NS-II cells are transformed to Nonself III (NS-III). In stage III, the NS-II cell excretes a protein, procoagulant (P), which in the presence of calcium ions is able to shortcut hemostasis on the cell surface by activating prothrombin. Procoagulant (P), catalyzes the conversion of prothrombin (PTH) to thrombin (TH). Thrombin catalyzes two reactions: the conversion of proenzyme Factor XIII (FXIII) to plasma transglutaminase Factor XIIIa (FXIIIa); and the conversion of fibrinogen (FG) to monofilamentous fibrin (MFF) over the NS-III site. Monofilamentous fibrin (MFF) has no three dimensional tensile strength. Therefore monofilamentous fibrin (MFF) is crosspolymerized by Factor XIIIa (FXIIIa) to a three dimensional, multilayered fibrin clot in situ and with Beta-2-microglobulin in the presence of calcium ions. The stable fibrin clots surround and camouflage the Nonself III (NS-III) transplantation antigen.

However, by reacting with the sulphydryl groups at the active site of cysteine proteinases, (i.e. transglutaminase enzymes and procoagulant), alpha-ketoaldehydes (KA) remove and prevent reformation of the fibrin "cover" over the transplantation antigenic sites. Without the protective coat, the "nonself" sites are exposed to foreign cell recognition and destruction by natural killer cells (NK) of the host's immune system represented in FIG. 2 as the "killed cell".

The role of transglutaminase in masking the nonself (antigenicity) of a mammalian fertilized egg so that it may successfully complete implantation, angiogenesis and placenta formation, has been well documented (Lampe, L., *Szuleszet nogyogyaszt,* (Obstetrics, Gynecology) Vol I p.6 Medicina Publisher, Hungary 1981). The egg becomes nonself upon cell fusion with the "effector" sperm (stage 1 of FIG. 2). The nonself conceptus is originally coated with uteroglobulin, a protein found in abundance between the 12th–18th days of menses in the uterus (stage 2). This covering then changes over to fibrin (stage 3) after fertilized egg is implanted. Fibrin formation around the fertilized cell is the result of local activation of hemostasis by a fertilized egg produced procoagulant. A layer, called Nitabuch's fibrin layer is present in the decidua even at the 36th week of pregnancy separating the conceptus from the mother. (Lampe L. in Szuleszet es nogyogyaszat (Obstetrics and Gynecology) Vol I p.96 Medicina Publisher, Hungary, 1981)).

The "two-step" masking procedure is also well documented in cancer cells. Normal cells become cancerous by interacting with an effector (e.g., carcinogens. UV radiation etc). In the first step of the camouflage (stage 2), altered "minimum deviation" cells pick up any protein available in the circulation and bind it to the newly developed antigenicity site via reaction with tissue transglutaminase. Once the altered cell becomes malignant, cancer procoagulant is produced. As depicted in stage 3 of FIG. 2, cancer procoagulant (P) activates hemostasis and fibrin is deposited over the cancer cell's transplantation antigens (Gordon, S.G., "Cancer Procoagulant," in Hemostasis and Cancer (ed. L. Muszbek) CRC Press, p. 19 (1987)).

A similar protein deposition sequence by tissue transglutaminase and procoagulant can be induced in cells attacked by agents which penetrate or attach to host cell membranes (e.g., bacteriums, viruses, fungi, etc.) or on the surface of free living, noncell-penetrating agents (e.g., parasites, fungi, bacteriums, etc.) used for their own defense.

In sum, once localized at a nonself cell, there are two modes by which latentiated alpha-ketoaldehydes attack in-vivo. In one mode, protein synthesis is inhibited thereby preventing growth and proliferation of the nonself cell. In the second mode, latentiated alpha-ketoaldehydes remove and prevent the reformation of the protective coating camouflaging nonself cells. Once this coating is removed, the nonself cells are exposed to recognition, attack and destruction by the host's natural killer cells.

Therefore, whereas with conventional chemotherapies, the patient's normal immune response is eliminated or reduced, chemotherapies based on alpha-ketoaldehydes actually enlist the patient's own immune response to recognize and destroy foreign cancer cells.

Utility

Latentiated alpha-ketoaldehydes, are useful in controlling any disease or condition resulting from the presence of nonself cells in a host. An advantage of using latentiated alpha-ketoaldehydes for treating diseases that result from the presence of nonself cells in a host is that this mode of treatment is resistant to mutations. This is because alpha-ketoaldehydes are found naturally in host cells and, therefore, do not initiate a defense mechanism in nonself cells. Administration of latentiated alpha-ketoaldehydes are especially useful in treating the following diseases, without limitation: cancer, viral diseases (e.g., AIDS, influenza, measles, mumps, chicken pox, shingles, hepatitis, diabetes), bacterial diseases (e.g., pneumonia, bronchitis, meningitis, carditis, periodontitis, bovine mastitis) and fungal diseases (e.g., histoplasmosis, blastomycosis, candiadiasis) all result from the infection and proliferation of nonself cells in a vertebrate host.

An advantage in using latentiated alpha-ketoaldehydes in treating diseases caused by the presence of nonself cells in a host is that latentiated alpha-ketoaldehydes can pass the blood/brain barrier. Thus, for example, latentiated alpha-ketoaldehydes would be useful in treating AIDS patients and in preventing the dementia that is frequently a symptom of the disease.

In addition, cancer results when a vertebrate's own cells become nonself. Therefore, latentiated alpha-ketoaldehydes could be used as an antineoplastic agent. Example 3 describes the effect that methylglyoxal (MG) and liposomal methylglyoxal (L-MG) have on tumor-bearing mice. Both MG and L-MG were found to be equally potent in topical treatment. However, L-MG was found to be far more effective in systemic treatment of tumors. Also, L-Mg treated tumor-bearing mice were found to be resistant to reformation of tumors. Apparently an immunity is also produced when cancer is treated with latentiated alpha-keto aldehydes. This immunity could prove important in preventing recurrence of cancer.

As an antineoplastic agent, latentiated alpha-ketoaldehydes can be used in place of surgery or after the surgical removal of a tumorous growth. Control and prevention of new metastases which may arise as a consequence of "surgical spilling" or already existing non-accessible metastases is possible.

Alpha-ketoaldehydes can further be used as a birth control device. At an early phase of embryonic development, fertilized eggs develop into a "trophoblast." The outer layer of a trophoblast consists of a monolayer of specialized cells whose function is to implant the developing embryo into the uterine wall, provide arterial and venous blood connections and to initiate formation of the placenta. These aggressive, fermentative and invasive cells are comparable to tumor cells in that they camouflage their outer surface with host protein.

Example 4 describes experiments showing that latentiated alpha-ketoaldehydes can be used in birth control. Daily administrations of latentiated alpha-ketoaldehyde to pregnant female mice resulted in 83.3% of the pregnancies being inhibited.

Latentiated alpha-ketoaldehydes are also useful as radiosensitizers. Experiments described in Example 5 show that administration of latentiated alpha-ketoaldehydes to a vertebrate host results in an increased effectiveness of radiation treatment by a factor of about 5 to 10. Therefore, administration of alpha-ketoaldehydes in conjunction with radiation treatment will permit lower radiation dosages and thereby reduce the effects of nausea and hair loss due to radiation treatment with therapeutic effects.

Latentiated alpha-ketoaldehydes can also be effective in influencing the "take" of transplanted tissues (e.g., skin, pancreas, liver, kidneys, heart, lung). Therefore, administration of latentiated alpha-ketoaldehydes can permit intra- and interspecies transplants. This is because the presence of alpha-ketoaldehydes in vivo inhibits protein synthesis and thus antigen-formation, which is responsible for the initiation of the rejection mechanisms. Administration of latentiated alpha-ketoaldehydes during and for a short period of time after transplantation (e.g., 60 days) would obviate the need for rejection fighting drugs. Latentiated alpha-ketoaldehydes could be administered as needed until the transplant or graft over time becomes "self."

Example 6 describes an experiment in which liposomal methlyglyoxal was administered intravenously to mice undergoing skin transplants. Pretreatment for 10 days prior to transplantation, followed by 25 days post transplant treatment resulted in no rejection of the graft on days 26–30 and 10% rejection on days 31–40. An interesting observation is that the tissue acceptance continued even after the biochemical was no longer administered. Apparently the use of the biochemical also permitted the foreign tissue to be "adopted".

Latentiated alpha-ketoaldehydes are further useful as anticoagulants. As explained in conjunction with FIG. 2, alpha-ketoaldehydes react with the sulphydryl groups of transglutaminase enzymes In so doing, the chemicals inhibit the formation of fibrin. Thus, latentiated alpha-ketoaldehydes administered in vivo into a vertebrate can be useful as a prophylactic against blood clot formation.

Example 9 describes an experiment showing the effect alpha-ketoaldehydes have on blood coagulation. Clotting times of alpha-ketoaldehyde treated plasma was compared to clotting times of control plasma. Chloromethylglyoxal and dichloromethylglyoxal were found to be the most effective anti-coagulants.

Alpha-ketoaldehydes are generally administered to vertebrate animals, including but not limited to fish, avians and mammals including humans. Effective treatment requires a steady, subtoxic blood level. This can be done by continuous administration. The compounds of this invention can be employed in admixture with conventional excipients, i e., pharmaceutically acceptable organic or inorganic carrier substances suitable for parenteral, enteral (e.g., oral) or topical application which do not deleteriously react with the active compounds.

Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., enzyme inhibitors, to further reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

For enteral application (including via oral and nasal mucosa), particularly suitable are tablets, dragees, liquids, drops, suppositories or capsules. A syrup, elixir or the like can be used wherein a sweetened vehicle is employed. For oral administration, the alpha-ketoaldehyde should be physically latentiated so that the alpha-ketoaldehyde is not released in the intestine and the stomach and there is controlled release at nonself cells. Latentiated alpha-ketoaldehydes may also be administered subcutaneously or transcutaneously.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc.

For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a Freon.

The average daily dose with liposomal methylglyoxal as determined with mice of 26g±2g body weight at dose levels of 260 mg/Kg mice is about 6.5 mg in 0.1 ml IV injectable. These values can be converted for other species by using a conversion chart which is based on the equivalent body surface, and this establishes the "body surface area-dose" relation (Freireich, E.J. et al., Can. Chem. Therap. Rep., 50:219 (1966)).

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations e.g., by means of an appropriate, conventional pharmacological protocol.

The present invention will now be illustrated by the following examples, which are not intended to be limiting in any way.

EXAMPLE 1

Production of Liposomal MethylGlyoxal (L-MG)

The lecithin-cholesterol-methylglyoxal ratio of the following liposomal methylglyoxal is 6:2:3 w/w/w (weight/weight/weight). The methylglyoxal and cholesterol contents are variable over a wide range. For example, the methylglyoxal content can vary from 0.5 to 4, while the cholesterol content may also vary from 0 to 3 weight ratios. The lecithin content, however, is not variable.

First, six grams of egg lecithin (Sigma) and 3 grams of cholesterol (Sigma) are dissolved in chloroform.

At this point either of the following two procedures can be used:

1. To the solution, 3 g of methylglyoxal in water (7.5 ml 40% aqueous solution Aldrich) is added and mixed. The water is removed from the mixture by repeated azotropic distillation in a vacuum at bath temperature (not exceeding 30° C.). The residue is taken up in chloroform and solvent evaporated as above. The steps are repeated 3-4 times so that all water is removed. To the resultant lipid film, containing the methylglyoxal, physiological saline is added, shaken by hand, sonicated (on ice for 9 min.; sonic power output 1500–2000 decibels) after the final volume is adjusted to 130 milliliter.

2. The chloroform is removed by vacuum distillation (bath temperature, 20° C.). To the resultant lipid film three grams of methylglyoxal (7.5 ml 40% aqueous solution, Aldrich) is added, and then diluted to 100 ml with physiological saline. The lipid film in the round bottomed flask is suspended into the water by handshaking, followed by sonication (on ice for 9 min.; sonic power output 150–2000 decibels) of the suspension. The final volume of the sonicate is adjusted to 130 ml with saline.

The sonicated liposome suspension is centrifuged at 10° C. for 2 hrs. (10,000 RPM). The supernate is collected and the amount of methylglyoxal present in the solution is estimated by Friedman's titration method (Friedman TFJ:JBC:73.331.1927). The precipitate is resuspended into 100 ml saline and centrifuged (60 min. at 10° C., 10,000 RPM). The collected precipitate is resuspended into saline at concentration required for in vivo treatment.

EXAMPLE 2

Production of Liposomal Phenylglyoxal (PhG)

The lecithin-cholesterol-phenylglyoxal ratio of the following liposomal phenylglyoxal is 6:2:2 w/w/w, (weight/weight/weight). Egg lecithin (360 mg), cholesterol (120 mg) and phenylglyoxal monohydrate (136 mg) are mixed and dissolved in chloroform. (Phenylglyoxal is soluble in chloroform methanol and ethanol and is sparingly soluble in water). The chloroform is removed by evaporation in a vacuum at room temperature, resulting in a thin film in the round bottomed flask.

The thin film containing the phenylglyoxal is mixed with 20 ml physiological saline, shaken by hand, and the resultant suspension is sonicated for 2 minutes on ice. The formed liposome suspension is centrifuged at 10° C. for 2 hours at 10,000 RPM. The supernate is collected and the phenylglyoxal present in the solution is estimated by Friedman's method. The amount of phenylglyoxal in the precipitate is calculated and it is resuspended in physiological saline at a required concentration and stored at room temperature. In a typical experiment 4 mg/ml phenylglyoxal is used for in vivo treatment.

The liposomes containing phenylglyoxal are stable for 5–6 days at room temperature. After longer storage, a precipitate is formed which can be resuspended on sonication.

EXAMPLE 3

In Vivo Treatment of Tumors with Physically Latentiated Methylglyoxal

Methylglyoxal which is equally soluble in both the aqueous and the lipid phase was encapsulated into liposomes of 8–20 microns in diameter as explained in detail in Example 1. Groups of mice were inoculated with Sarcoma-180 cells either subcutaneously (sc) or intraperitoneally (ip) (3 million cells; 89% viability) followed by intravenous (iv) or intraperitoneal treatment with methylglyoxal (MG) or liposome encapsulated methylglyoxal (L-MG) (10 days, 260 mg/Kg per mouse per day, Table 1).

TABLE 1

| S-180 cell inoculation treatment | ip ip (topical) | | sc iv (systemic) | |
|---|---|---|---|---|
| | T/C % | I% | T/C % | I% |
| control | 100 | 0 | 100 | 0 |
| MG | 0.0043 | 99.9 | 87.6 | 12.4 |
| L-MG | 0.0052 | 99.9 | 4.0 | 96.0 |

Note: T/C % = (test/control) × 100 and I % = 100 − T/C % (I % is the inhibition of tumor growth)

MG and L-MG were found to be equally potent in topical treatment. However, L-MG was found to be far more effective than MG in systemic treatment of tumors. By this method of physically latentiating methylglyoxal, an increased amount of alpha-ketoaldehyde was delivered to target tumor cells.

Physico-pathological examination of tumor-bearing mice treated with liposome encapsulated methylglyoxal (L-MG) shows an initial and very rapid increase of leucocytes in the circulating blood and in the tumor areas. This probably reflects a rather sharp activation of the reticulo-endothelial-system (RES) which results in the mass destruction of malignant cells. The leucocytes continue to accumulate and result in a rapid necrosis of cancerous cells. The appearance of a reactive granulation tissue replaces the cell debris. These phenomena are absent in non-tumorous control subjects.

L-MG treated tumor-bearing mice also have enlarged spleens due to the marked increase of hematopoeitic activity including an increased number of megakaryocystes and normoblasts within the red pulp. Leucocyte formation was also occasionally observed in such secondary sites, as the liver and kidneys. However, the pancreas, liver, lung, skin and muscles appeared normal. In most cases, a violaceous and homogenous material was found within the tubules of the kidneys. This damage is probably due to the inadequate excretion of the metabolic products under semi-anuric conditions. Administration of diureticums or mannitol may rectify this condition.

Sarcoma-180 cells were then injected (s.c. or i.p.) into L-MG treated tumor-bearing mice. However, these cells did not develop into tumors.

EXAMPLE 4

Preventing Pregnancy in Mice by Administrating Latentiated Alpha-ketoaldehyde

Six 5 month old female CD-1 mice were injected intraperitoneally with N-1 hydroxy acetonyl maleimide for 12 days (50 microgram/ 20 g mice in saline: max volume 0.6 ml/A/D). Another group of the same mice were injected intraperitoneally with saline for 12 days (0.4ml). this second group of mice served as the control.

Two experienced males were introduced to each group of females and kept together for 8 days during which time the females received their daily injection. Copulation plugs were seen on each female by the 12th day of injection, and signs of pregnancy were seen on the control females on the 15–16th day of the experiment. The females delivered on 20–23 (control) and 24–27th (treated) day respectively (Table 3).

TABLE 3

|  | Control<br>12 female | Test<br>12 female |
|---|---|---|
| delivered | 106 (12 female) | 11 (2 female) |
| T/C % | 100 | 10.3 |
| I % | 0 | 89.7 |
| male/female ratio of the pups: 45% male, 55% female | | |
| normal values: | | |
| gestation |  | 19–21 days |
| estrus duration |  | 2.5 days |
| trophoblast formation |  | 4–5 days |
| implantation on |  | 4–6 days |

The experiment was repeated with the same females two months later, except that females of the control group were assigned to the test group, while females of the test group were reassigned to the control group. The result of the second experiment showed 83.3% inhibition of delivery by the treated females. The control group delivered 102 pups (T/C = 100%).

Results

Latentiated methylglyoxal inhibits implantation of fertilized mouse eggs. Two mice delivered a reduced size litter: these females probably had a delayed ovulation, which is apparently quite common among mice. The treatment had no effect on the reproductive cycle of the females.

EXAMPLE 5

Radiation Enhancement

Thiol containing compounds protect cells against ionizing radiation damage. Therefore, compounds that reduce the free —SH content of cells make them more susceptible to radiation damage. Ashwood-Smith reported in a series of papers (i.e., [J. Radiat. Biol., 15:285 (1969)] that the sensitivity of bacteria and mammalian cells towards gamma irradiation can be significantly increased by decreased thiol content.

Experiments conducted in vitro concur with their findings: Mice carrying ascitic Sarcoma-180 cells (20 million) were injected with liposomal methylglyoxal (120 mg/kg mouse). Ten minutes after the injection the mice were irradiated with a gamma source (612 RAD equivalent of 400 R total body radiation; calculated lethaldose:LD-50/30 days). The treatment was repeated 3 times 4 days apart. Positive controls were subjected to treatment with methylglyoxal or radiation alone. One day after the last radiation, the animals were sacrificed, the ascitic fluid was collected and the malignant cells were counted.

TABLE 4

|  | TC % | I % | P % |
|---|---|---|---|
| control | 100 | 0 | 0 |
| MG (alone) | 104.7 | na | 4.7 |
| RAD (alone) | 36.9 | 36.8 | na |
| RAD + MG | 7.7 | 92.3 | na |

RAD = Radiation, MG = methylglyoxal
P % = Promotion %; I % = inhibition %

EXAMPLE 6

Combatting Rejection Mechanism

The experiments described here were performed on random-bred Swiss albino mice (white, females, average body weight 26±3 g; Charles River CD-1-strain) and inbred C3HStCrl mice (cinnamon gray, females, average body weight 10°2 grams; Charles River pedigreed breeders from L.C. Strong Foundation) and othotopic skin transplants were made in both ways, that is, white to gray and gray to white.

Standard transplantation technique (Billingham, R.E. and W.K. Silvers in Transplantation of Tissues and Cells, The Wistar Institute Press, Philadelphia, p. 8, (1961)) was utilized: From nembutal anesthetized animals 4–6 "pinch" -grafts (full thickness, 3–4 mm in diameter) of the close clipped and sterilized skin were collected from the thorax and immediately transplanted. The grafts were positioned in the "beds" (in place of the pinch-graft) and were held in position by tulle gras (vaseline-impregnated gauze) and by plaster-of-Paris impregnated bandage around the thorax.

The bandages were removed on the 6–9th day after the transplantation and the future development of the grafts was followed by macroscopical observations.

Positive and negative controls were made simultaneously for skin rejection:
1. Four positive control isografts (white to white, and gray to gray) were made. They showed a confluence and union of the fitted grafts with the surrounding skin and beds in 7–10 days. On the 21–28th day the fur-bearing skin had regenerated a completely new crop of hairs indistinguishable from the original population with respect to colors, density and orientation.

2. Four negative control heterografts (white to gray and gray to white) were made without treatment. They showed no confluence and union with the surrounding tissue which was locally inflamed. On the 10–12th day after transplantation, intravascular thrombies, capillary ruptures, extravasation of blood were the first signs that the grafts were heading for necrosis and rejection which occurred on the 18–25th day.

The heterografts with treatment followed three courses with liposomal methylglyoxal (at dose level 3.744 mg/kg/animal/day) administered intravenously in a total amount of 1.0 ml/animal/day.

a. Animals were treated for 10 days with the composition before grafts were exchanged and treatment was discontinued on the day of transplantation.
b. Animals were not treated before the grafts were exchanged but the treatment started on the day of transplantation and continued for 10 days.
c. Animals were treated for 10 days with the drug before the grafts were exchanged and the treatment schedule was continued for 25 days after the transplantation.

TABLE 5

| Assay | No of mice | Graft* | Treatm+ | Results |
|---|---|---|---|---|
| Positive control | 10 | w to w | no | 100% take in 21–28 days |
|  | 10 | g to g | no |  |
| Negative control | 10 | w to g | no | 100% rejection in 10–25 days |
|  | 10 | g to w | no |  |
| (a) |  |  |  |  |
| Pretreatm. for 10 days | 10 | w to g | yes | 30% rejection on 26–30 days |
|  | 10 | g to 2 | yes | 100% rejection on 31–40 days |
| (b) |  |  |  |  |
| Post graft treatm. for 10 days | 10 | w to g | yes | 10% rejection on 26–31 days |
|  | 10 | g to 2 | yes | 10% rejection on 31–40 days |
| (c) |  |  |  |  |
| Pretreatm. for 10 days | 20 | w to g | yes | No rejection on 26–30 days |
| and post graft treatm. for 25 days | 20 | g to w | yes | 10% rejection on 31–40 days |

+Treatment: daily injection with 3.744 mg/kg methylglyoxal-malcimide in 1.0 ml saline by intraperitoneal route/mouse/day
*The w stands for white mice (Swiss albino, randombred, Charles River CD-strain. The g stands for cinnamon gray mice (C3HStCrol, inbred strain)
NOTE: per cent figures in Results are cummulative values.

EXAMPLE 7

Effect of Anphaketoaldehyde (KA) on the Proliferation of Molds (fungi) in Vitro (1) Stock solutions in 26% 2 popanediol:

| Methylglyoxal | (MG) | (mol wt: 72.06) | 0.958 M |
|---|---|---|---|
| Chloromethylglyoxal | (CMG) | (mol wt: 106.51) | 0.995 M |
| Dichloromethyl-glyoxal | (DCMG) | (mol wt: 140.45) | 0.854 M |

(2) Microorganisms:
Penicillum notatum
Aspergillus niger

Note: Many L. penicillium, a genus of molds, are sometimes found as parasites on man (i.e.: P.montoyai, P. buffardi, P. minimum etc), others like P.notatum, are used in cheese industry.

L. aspergillus, a genus of ascomycetous fungi, includes several of the common molds. Some of them are like A. auricularis, A. barbae, A. mucoroides etc.). A. niger found in the external ear causing otomycosis. It also causes diseases in animals that consume grain infected with it.

(3) Assay: The microorganisms were grown in Saburand's dextrose agar (Scott) at 35 C for stock cultures. For assay the spores were plated on Mueller-Hilton agar plates (7cm dia). The test compounds were applied to the plates on sensi disks (6 mm dia, Whatmann #17 paper) in volumes of 10, 20, 30, 40 microliter made up to 40 plating volume of microliter with the solvent. The plates were incubated at room temperature and in the dark for 40 hrs. The diameter of the inhibition ring around the sensi disks were measured.

| | Results: | | | |
|---|---|---|---|---|
| | 10 | 20 | 30 | 40 |
| | | | microliter KA | |
| | Penicillin | | | |
| MG | — | — | 8 | 10 |
| CMG | 8 | 10 | 12 | 14 |
| DCMG | 8 | 10 | 13 | 16 |
| | Aspergillus | | | |
| MG | — | — | 7 | 9 |
| CMG | 8 | 11 | 17 | 22 |
| DCNG | 10 | 12 | 14 | 15 |

REMARK

With penicillin: strong growth, sharp edged, clear inhibition zones. With aspergillus: strong growth, somewhat "fuzzy" edged, clear inhibition zones.

The inhibition rings with CMG and DCMG remained unchanged in the highest concentration for 8 days. By this time the penicillin plate developed a second ring around the inhibited area: a white zone averaging to 10–15 mm diameter. Under the microscope, it was seen that the spore formation in this area was inhibited while mycelium development was not. Since the rest of the plate was colored dull green indicating spores are present, the mycellium and spore development of this fungus show different sensitivity towards methylglyoxal (MG).

EXAMPLE 8

Effect of Alpha-Ketoaldehyde on the Proliferation of Candida Albicans

Candida albicans (C. cerviceae) is a yeast present in over 90% of normal human GI tract. The number is kept relatively constant by the immune surveillance system (ISS). Moreover, immune supressors, like antineoplastic drugs, often cause generalized candidiasis of immune compromised patients: 15.35% of leukemic patients die of candidiasis. Other cancers also have high C. albicans infection as a cause of death.

Candidias are very potent yeasts that will adapt to most conditions readily. They are quite refractory to antibiotics. 5-fuloro cytosin (5FC), a potent agent has but a shortlived action: it penetrates the cell wall of the albicans but not human cells. Thus it exhibits low toxicity to the host, while after a short lived action the albicans adapt.

The candida albicans used for this experiment was obtained from Dr. Scott, Hoffmann La Roche.

(A)

1. Stock Solutions

Stock solutions of the following test compounds were dissolved in physiological saline. However DOV was dissolved in water.

|  | μmole/10 μl |  |
|---|---|---|
| MG | 2.22 | methylglyoxal |
| CMG | 1.09 | chloromethylglyoxal |
| DCMG | 1.11 | 3, 3 dichloro-methylglyoxal |
| AcMG | 12.7 | 3-acetyl methylglyoxal |
| MGMALI | 0.964 | N-hydroxyacetonyl maleimide |
| KE | 4.3 | kethoxal |
| DOV | 4.8 | 2, 4-dioxovaleric acid |
| MALI | 0.945 | maleimide |
| PhG | 0.10 | phenylglyoxal (limit solubility) |
| 5FU | 0.43 | 5 fluorocytosine |
| AMP-B | 0.956 | amphotericin-B |

2. Activity Assay

C. albicans isolated from clinical specimens were density grown in SubbaRow's broth at 35 C. A loopful of yeast suspension was evenly spread on the surface of Muller-Hilton agar plates (7cm diameter) with a sterile cotton applicator and incubated for 12 hours. The test compounds were placed on the surface of the sensidisks (Whatmann No. 17 paper, 6mm diameter) in a volume of 5, 10, 20, and 50 μliter of stock solutions and made up a final volume of 50 μliter with saline. The plates then were placed and kept at 37 C for 24 hours (*) and 48 hours (**) when the diameters of the inhibitory rings were recorded. Photographs were also taken of plates.

| 3. Results: | | | | |
|---|---|---|---|---|
|  | μliter test compounds | | | |
|  | 5 | 10 | 20 | 50 |
|  | mm inhibition diameters | | | |
| MG | | | | |
| * | — | — | 8 | 10 |
| ** | — | — | — | — |
| CMG | | | | |
| * | — | 7 | 21 | 33 |
| ** | — | — | 10 | 31 |
| DCMG | | | | |
| * | — | 8 | 20 | 32 |
| ** | — | — | 17 | 29 |
| AcMG | | | | |
| * | — | 18 | 31 | 34 |
| ** | — | 11 | 24 | 30 |
| MGMALI | | | | |
| * | — | 8 | 18 | 22 |
| ** | — | — | 17 | 22 |
| KE | | | | |
| * | — | 7 | 17 | 25 |
| ** | — | — | 16 | 24 |
| DOV* | negligible | | | |
| MALI | | | | |
| * | — | 13 | 21 | 29 | 30 |
| ** | — | — | 17 | 25 | 30 |
| PhG | | | | |
| * | — | — | 5 | 8 |
| ** | — | — | — | — |
| MALI+* CMG | 29 | 34 | 40 | 42 |
| MALI+* DCMG | 37 | 32 | 38 | 40 |
| 5FC* | 33 | 45 | 50 | 55 |
| AMP-B* | — | — | 2 | 5 |

(B). Inhibition of C. albicans

1. Stock Solutions

Same as above.

2. Activity Assay

Stock cultured C. albicans is used. The yeast isolated from clinical specimens was stock cultured (subcultured) on semisolid trypsoy agar plates. A loopful of microorganism was transferred to SubbaRow's broth (SRB, 5ml) and the rate of growth was observed for 12, 24, and 48 hours at 36 C. Equally good growth rate was observed with subcultures at any incubation time. Thus, from the subculture(s), transfers were made every 48 hrs into SRB to keep the experimental strain available for assays. From the 24–48 hrs SRB cultures a loopful of turbid solutions was transferred and spread on either (a) trypsoy agar plates or (b) EBM agar plates which were fortified with horse and calf serum and incubated at 36 C for 24–48 hrs. Plate culture on (a) showed strong growth in 24 hrs while (b) plate supported only slight growth even at 48 hrs. Plate (a) was selected for growth inhibition assay(s) with ketoaldehydes.

One milliliter of SRB culture (24–48 hrs growth) was mixed with 10 ml trypsoy agar, warmed to 38 C and rapidly poured into sterile Petri dishes (7cm), spread evenly and allowed to solidify. The selected test compounds (in 30 μl total volume, as above) were placed in sensidisks (6mm dia, Whatman #17) on the infected agar surface. The plates were incubated for 24 hrs at 37 C. The extent of inhibition, clear zones around the sensi disks, were measured and recorded. In some cases contact photorecords were also made with the plates. (The dark zones on the photos are the inhibition (no growth) areas of C. albicans.

These assays were aimed at finding the variations of inhibition due to (i) the variable amount of yeast in (ii) a three dimensional area of the plates. Each result is the statistical mean of twenty assays on different batches of C. albicans.

| mm Inhibition Diameters (30 μl test, 24 hrs incubation) | | |
|---|---|---|
| MG | 6.0 | s +/− 2 |
| CMG | 26.6 | s +/− 4.5 |
| DCMG | 23.0 | s +/− 4.1 |
| AcMG | 25.3 | s +/− 7.1 |

(Note: s +/− is the standard deviation)

Notes: with heavy inocculum the inhibition effects show up well in 24 hrs. With the light inocculum, although inhibition shows very little or no "regrowth" (transient inhibition), the relatively slow growth of C. albicans require an extension of incubation time to up to 4 days (when background gets uniform).

EXAMPLE 9

The Effects of Alphketoaldehydes on Blood Coagulation

(1). Assay 200 microliter thromboplastin (Ortho) was mixed with 10 microliter ketoaldehyde (KA) stock solution. Then 100 microliter citrated human blood plasma was added and the clot formation time (in seconds) was measured on a Fibrionometer. The effect of the ketoaldehyde on coagulation time was evaluated by comparing the clotting time of the KA treated plasma with the untreated control. The result (d%) was read from a special chart expressing the clotting activity.

All measurements were run in triplicates. The assay was run at 37 C (waterbath) in special tubes and all solutions were prewarmed.

(2). KS Stock Solutions: - in Physiological Saline methylglyoxal (MG) 0.988 M
chloromethylglyoxal (CMG) 0.940 M
3, 3-dichloromethylglyoxal (DCMG) 0.551 M
3-acetylmethylglyoxal (AcMG) 0.890 M
Phenylglyoxal (PhG) 0.694 M
3-Phenylmethylglyoxal (PMG) 0.856 M

(3). Assays (i) The plasminogen and ketoaldehyde were kept for 1-2 seconds before the blood plasma was added.

RESULTS:

|  | seconds coagulation time | d % | clot |
|---|---|---|---|
| control | 24 | 22 | hard |
| MG | 25 | 20 | hard |
| CMG | >200 | infinite | no |
| DCMG | >200 | infinite | no |
| AcMG | 21.5 | 28 | hard |
| PMG | 36 | 10.5 | hard |
| PhG | 35 | 11 | hard |

(ii) The plasminogen and KA were incubated for varying time before the blood plasma was added.

RESULTS:

(a) With plasma from a patient with prothrombin (clotting time 26 sec d % = 19. "Normal" (healthy) blood plasma clotting time 10-12 sec d % = 100)

RESULTS:

|  | incubation time seconds | clotting time | d% |
|---|---|---|---|
| MG | 30 | 39 | 15 |
|  | 60 | 32 | 13 |
|  | 130 | 39 | <10 |
|  | 190 | 41 |  |
|  | 300 | 91.8 |  |

(b) with normal plasma: clotting time = 11. 7 sec

| | d % = 100 | | |
|---|---|---|---|
| MG | 5 | 12.9 | 96 |
|  | 60 | 14.9 | 55 |
|  | 129 | 15.4 | 53 |
|  | 240 | 19.0 | 35 |
|  | 360 | 26.9 | 26 |
|  | 600 | >167.0 |  |
| CMG | 15 | 19.4 | 33 |
|  | 100 | >178.0 |  |
| 10x diluted DCMG | 10 | 13.5 | 37 |
| DCMG | 15 | >170.0 |  |
| 10x diluted | 10 | 12.9 |  |
| 20x diluted | 30 | 20.0 | 14.7 |
| AcMG | 120 | 13.9 | 78 |
| PhG | 120 | 19.5 | 33 |
| PMG | 120 | 21.2 | 28 |
| control | (end of assay) | 13.6 |  |

(c) A trial assay where blood plasma was replaced with whole blood (control = 14.9 sec    d % = 100)

|  |  |  |
|---|---|---|
| MG | 70 | 16.5 |
|  | 150 | 19.4 |
|  | 180 | 20.0 |
|  | 240 | 22.0 |
|  | 360 | 24.0 |

Equivalents

Those skilled in the art will recognize, or be able to ascertain using no more than routine experimentation, many equivalents to the specific embodiment of the invention described specifically herein. Such equivalents are intended to be encompassed in the scope of the following claims.

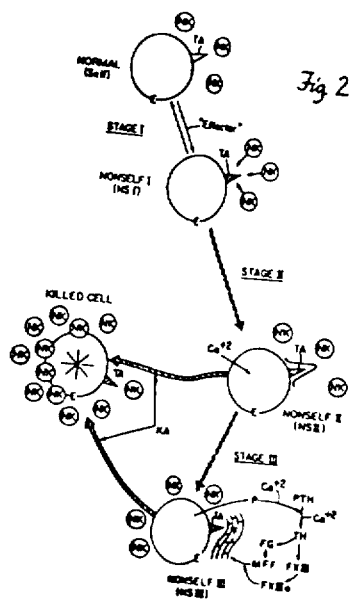

I claim:

1. A composition comprising an alpha-ketoaldehyde incapsulated in the lipid phase of a liposome, whereby its CO—CHO group extends outward from the exterior surface of the liposome, and a therapeutic compound encapsulated in the aqueous phase of the liposome.

2. A pharmaceutical composition comprising an alpha-ketoaldehyde incapsulated in the lipid phase of a liposome, whereby its CO—CHO group extends outward from the exterior surface of the liposome, a therapeutic compound encapsulated in the aqueous phase of the liposome and a pharmaceutically acceptable carrier.

3. A composition comprising an alpha-ketoaldehyde incapsulated in the lipid phase of a liposome, whereby its CO—CHO group extends outward from the exterior surface of the liposome.

4. A pharmaceutical which comprises the liposomes of claim 3 in a pharmaceutical composition carrier.

5. A pharmaceutical of claim 4 wherein the pharmaceutical composition carrier is compatible with topical application.

* * * * *

UNITED STATES PATENT AND TRADEMARK OFFICE
CERTIFICATE OF CORRECTION

PATENT NO. : 5,147,652
DATED : September 15, 1992
INVENTOR(S) : EGYUD

It is certified that error appears in the above-indentified patent and that said Letters Patent is hereby corrected as shown below:

The title page, should be deleted to replaced with attached title page.

United States Patent [19]

Egyud

[11] Patent Number: 5,147,652
[45] Date of Patent: Sep. 15, 1992

[54] AUTOBIOTICS AND THEIR USE IN ELIMINATING NONSELF CELLS IN VIVO

[75] Inventor: Laszlo G. Egyud, Woods Hole, Mass.

[73] Assignee: Cell Research Corporation, Newton, Mass.

[21] Appl. No.: 547,983

[22] Filed: Jul. 3, 1990

[51] Int. Cl.⁵ .......................................... A61K 37/22
[52] U.S. Cl. .................................. 424/450; 436/829; 514/675; 514/693
[58] Field of Search ................ 424/450, 489, 451; 514/693, 675; 568/420; 436/829

[56] References Cited

U.S. PATENT DOCUMENTS

| | | | |
|---|---|---|---|
| 4,066,650 | 1/1978 | Egyud | 260/281 G |
| 4,241,046 | 12/1980 | Papahadjopoulos | 424/19 |
| 4,440,740 | 4/1984 | Fix et al. | 424/1.1 |
| 4,529,561 | 7/1985 | Hunt | 264/4.3 |
| 4,844,904 | 7/1989 | Hamaguchi | 424/450 |
| 4,861,588 | 8/1989 | Neurath | 424/89 |
| 4,906,477 | 3/1990 | Kuyono et al. | 424/450 |

FOREIGN PATENT DOCUMENTS

86/01102  2/1986  PCT Int'l Appl.

OTHER PUBLICATIONS

Nozawa et al. J. Pharma. Sciences 70, p. 385 (1981).
Underwood Proc. Soc. Exp. Biol Med 100, 312 (1959).
Apple Cancer Chemotherapy Reports 52, 687 (1968).
Schenk Pharmazie 45, 747-9 (1990) Abstract.
Arndt. Oncology 44, 257 1987 Abstract.
Apple & Greenberg, *Cancer Chemotherapy Reports*, 52: 687-696 (1968).
Egyud & Szent-Gyorgi, *Science*, 160: 1140 (1968).
Underwood & Weed, *Proc. Soc. Exp. Biol. Med.* 83: 421-424 (1956).
Tiffany et al., *J. Am. Chem. Soc.*, 79: 1682 (1957).
Nozawa and Fox, *J. of Phar. Sciences*, 70: 385 (1981).
Thornalley, *Biochem., J.*, 269: 1-11 (1990).

Primary Examiner—Thurman K. Page
Assistant Examiner—G. S. Kishore
Attorney, Agent, or Firm—Hamilton, Brook, Smith & Reynolds

[57] ABSTRACT

Physically and chemically latentiated autobiotics are described. The latentiated autobiotics are useful for the treatment or prevention of any disease or condition, which results from the presence of nonself cells in a vertebrate host. Latentiated autobiotics are furthermore useful in suppressing immune rejection processes, as radiosensitizers and as anticoagulants.

5 Claims, 2 Drawing Sheets

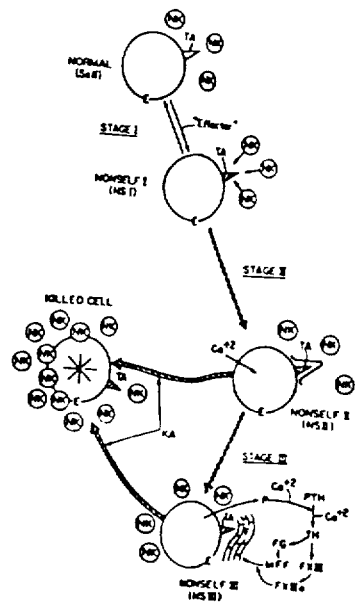

UNITED STATES PATENT AND TRADEMARK OFFICE
CERTIFICATE OF CORRECTION

PATENT NO. : 5,147,652

DATED : September 15, 1992

INVENTOR(S) : Laszio G. EGYUD

It is certified that error appears in the above-indentified patent and that said Letters Patent is hereby corrected as shown below:

The drawing sheet, consisting of Figure 1, should be deleted to be replaced with the drawings sheet, consisting of Figure 1, as shown on the attached page.

The drawing sheet, consisting of Figure 2, should be deleted to be replaced with the drawings sheet, consisting of Figure 2, as shown on the attached page.

Signed and Sealed this

Thirty-first Day of May, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,147,652

DATED : September 15, 1992

INVENTOR(S) : Laszio G. Egyud

Page 4 of 5

It is certified that error appears in the above-identified patent and that said Letters Patent is hereby corrected as shown below:

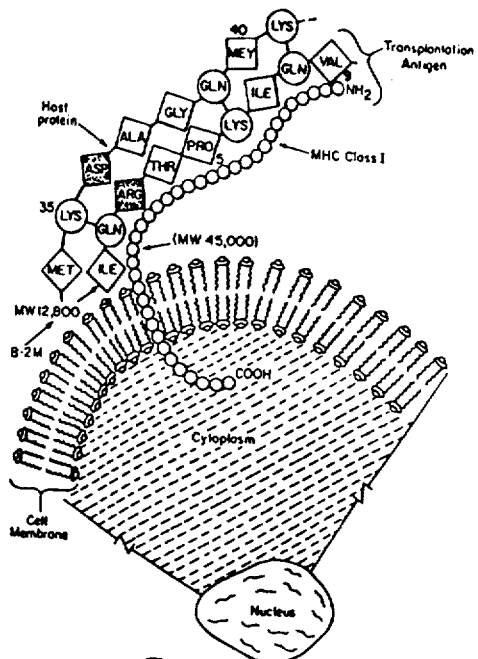

Fig. 1

UNITED STATES PATENT AND TRADEMARK OFFICE
CERTIFICATE OF CORRECTION

PATENT NO. : 5,147,652

DATED : September 15, 1992

INVENTOR(S) : Laszio G. Egyud

It is certified that error appears in the above-indentified patent and that said Letters Patent is hereby corrected as shown below: